United States Patent [19]

Harris

[11] 4,306,560

[45] Dec. 22, 1981

[54] SUTURE FORMING TOOL FOR SECURING AN ELECTRODE TO GENERALLY INACCESSIBLE BODY TISSUE

[75] Inventor: Donald L. Harris, Miami Beach, Fla.

[73] Assignee: Cordis Corporation, Miami, Fla.

[21] Appl. No.: 119,875

[22] Filed: Feb. 8, 1980

Related U.S. Application Data

[63] Continuation of Ser. No. 923,021, Jul. 10, 1978, abandoned, which is a continuation-in-part of Ser. No. 779,686, Mar. 21, 1977, Pat. No. 4,103,690.

[51] Int. Cl.³ .............................................. A61N 1/00
[52] U.S. Cl. .............................. 128/303 R; 128/419 P
[58] Field of Search ........... 128/303 R, 334 R, 419 P; 227/83

[56] References Cited

U.S. PATENT DOCUMENTS 2,960,895  11/1960  Hausknecht ......................... 227/83

FOREIGN PATENT DOCUMENTS 1248808  8/1971  United Kingdom ............ 128/334 R
1358466  7/1974  United Kingdom ............ 128/334 R

*Primary Examiner*—William E. Kamm
*Attorney, Agent, or Firm*—Kenway & Jenney

[57] ABSTRACT

A suture forming surgical tool particularly useful in attaching an epicardial pacer electrode to the heart. The tool has an elongate body and a manually operable plunger slidable in the body. The electrode is releasably secured to a distal end of the tool. In a first portion of its travel, the plunger acts on a pair of pusher wires that each drive lengths of malleable sutures through tubular dies that have curved central bores which impart curvatures of essentially predetermined radii to the sutures. As the curved sutures are ejected from the dies they pass through the adjacent heart tissue and form circular loops which securely attach the electrode to the heart. In a second portion of its travel, the plunger detaches the electrode and its lead wire from the tool.

11 Claims, 12 Drawing Figures

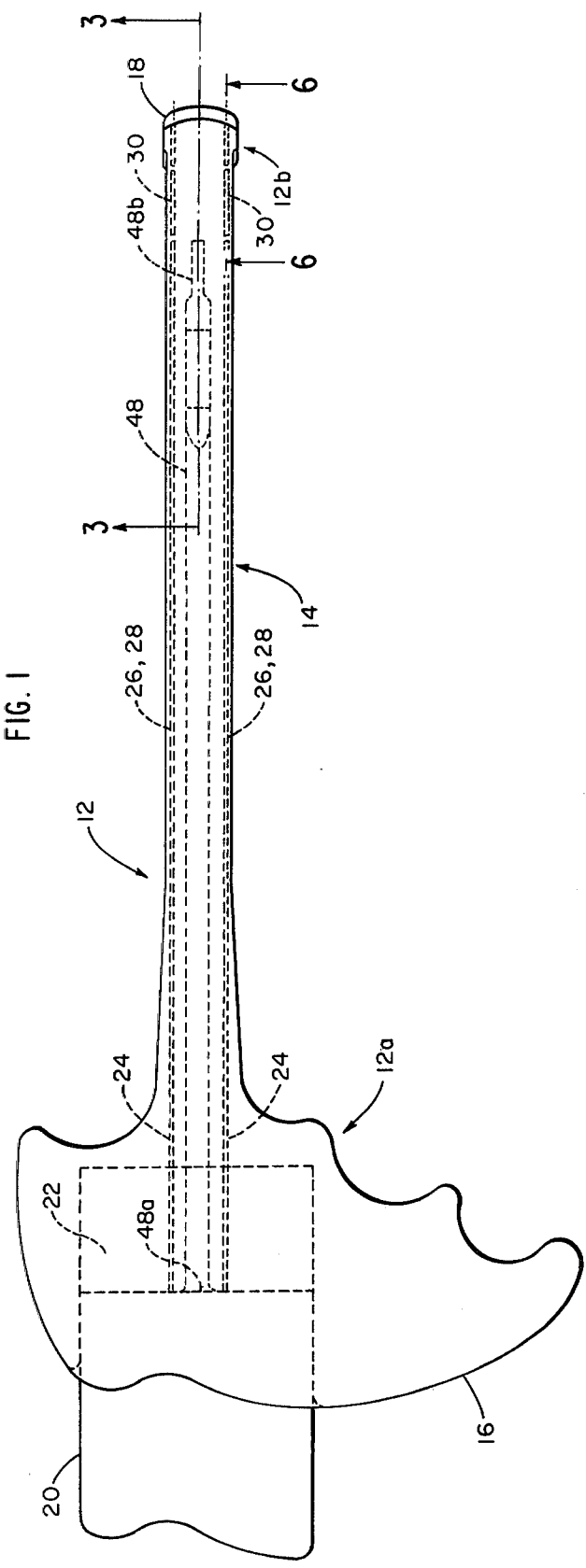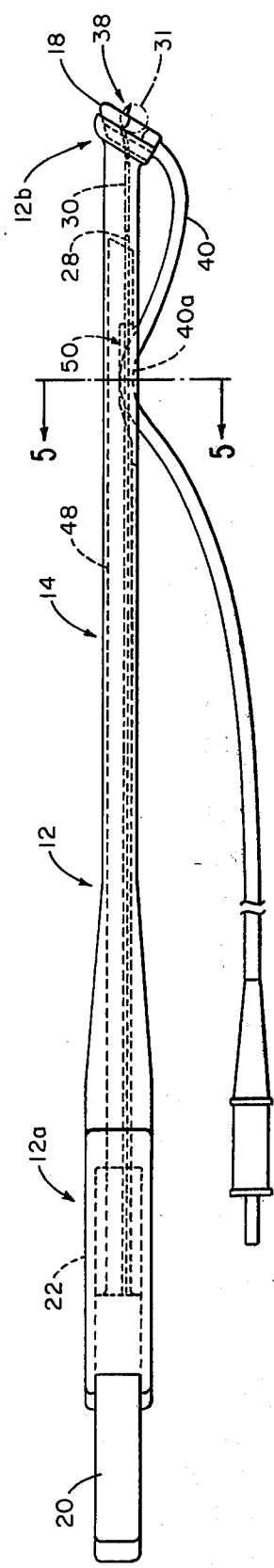

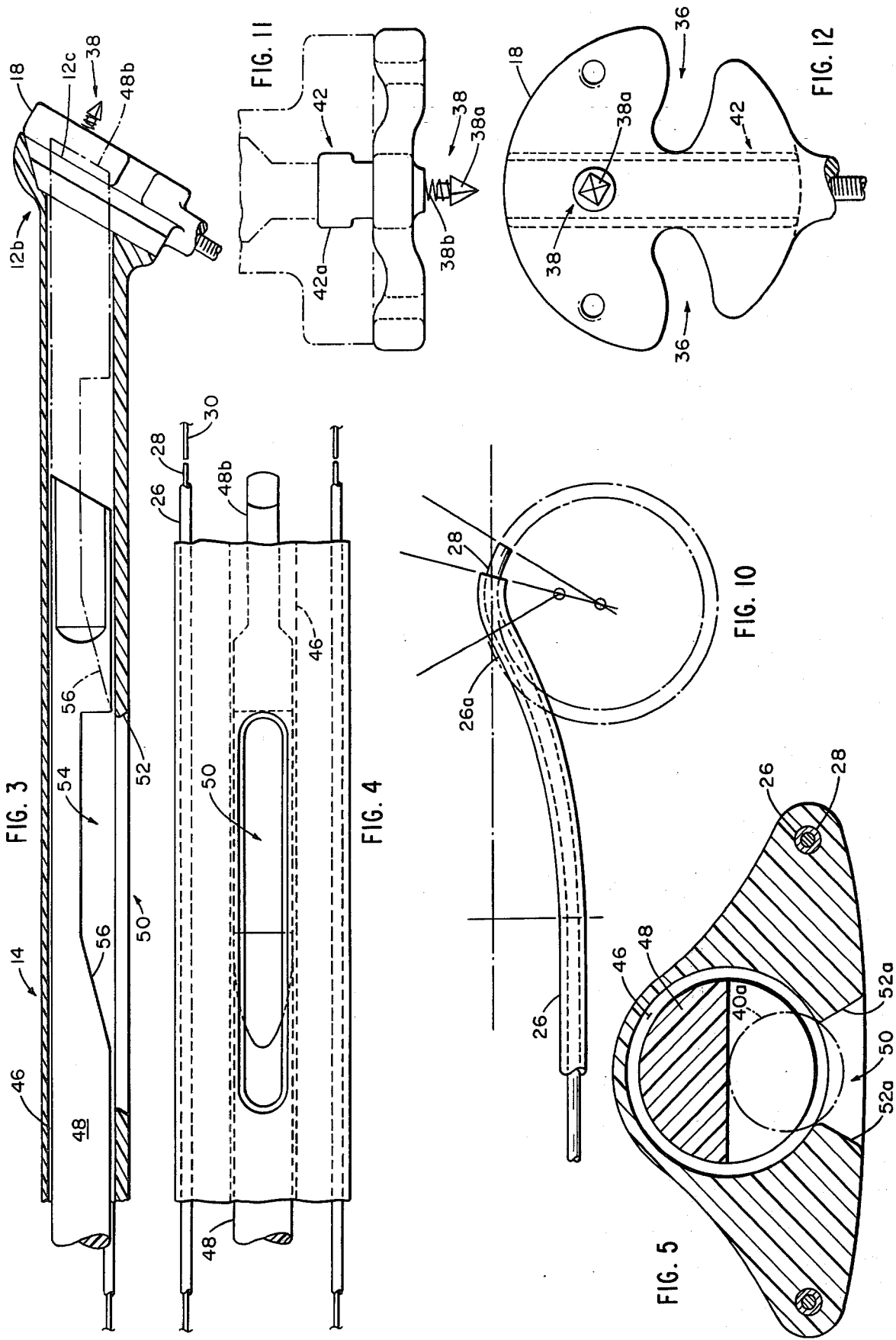

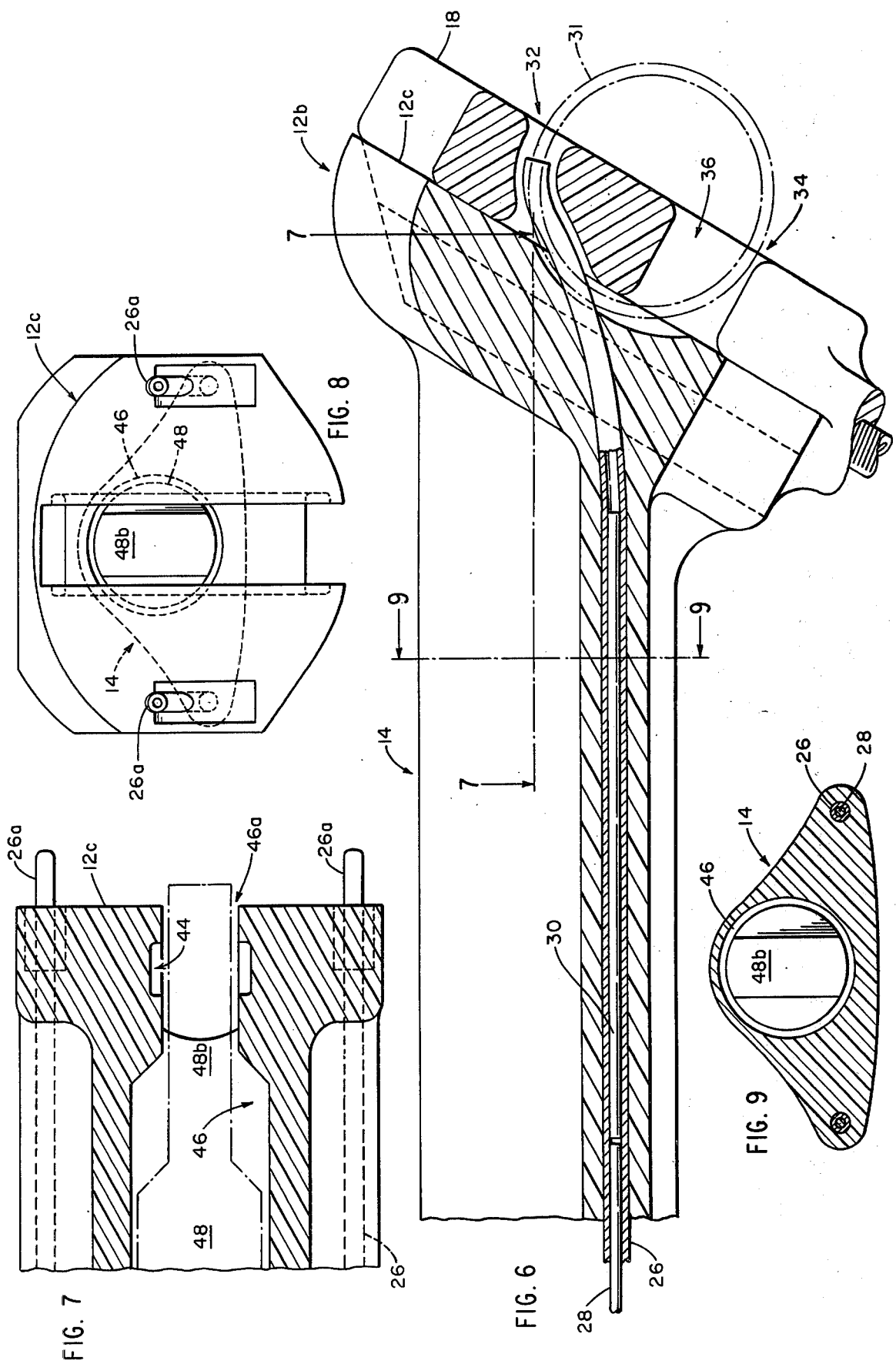

SUTURE FORMING TOOL FOR SECURING AN ELECTRODE TO GENERALLY INACCESSIBLE BODY TISSUE

This is a continuation, of application Ser. No. 923,021, filed July 10, 1978 now abandoned which in turn is a continuation-in-part of U.S. application Ser. No. 779,686, filed Mar. 21, 1977 now U.S. Pat. No. 4,103,690.

BACKGROUND OF THE INVENTION

This invention relates to suture forming surgical apparatus and more particularly to a surgical tool for suturing an epicardial pacer electrode to heart tissue.

Heretofore, a pacer electrode was attached to a heart by either conventional suture techniques that require a thoracotomy to expose the heart or by constructing the electrode to provide its own means of attachment and usually directing it to the heart through a vein. Both of these approaches, however, have disadvantages. A thoracotomy requires a large incision in the chest or thorax and carries with it the high risks associated with any such drastic surgery. Electrodes with their own means of attachment, for example the corkscrew-like device described in U.S. Pat. No. 4,000,745, traumatize the heart at the point of electrical stimulation. Trauma, in turn, causes scar tissue to form. Because scar tissue is a poor electrical conduction medium, more current is needed to properly stimulate the heart and the current requirements may vary with time. U.S. Pat. No. 4,066,085 to Hess describes a resilient epicardial electrode with prong-like attachment hooks separate from an electrical stimulating coil. While this device minimizes the trauma at the point of electrical stimulation, it must be inserted directly using forceps or the like. This requires drastic surgery to provide access for the implantation. U.S. Pat. Nos. 3,754,555; 3,902,501 and 3,814,104 describe known pervenous, endocardial electrodes where manipulation of the electrode after it is positioned in the heart release hooks, tines or prongs to secure the electrode.

More broadly, various surgical tools have been devised to facilitate the suturing of tissue in hard to reach locations. U.S. Pat. No. 1,822,330, for example, describes a tool that sutures tissue within the oral cavity during a tonsilectomy. The tool is inserted through a natural body opening and guided visually. Other suturing devices join easily accessible tissue by means of preformed metal clips or staples as described in U.S. Pat. Nos. 715,612; 2,881,762 and 3,098,232. None of these known suturing devices, however, can suture tissue that cannot be reached or viewed through a natural body opening or directly after exposing the tissue through surgery. Also, none of these known devices are adapted to support, position and suture an electrode on the heart, particularly where the suture is a closed loop and is removed from the point of electrical stimulation.

It is therefore a principal object of this invention to provide a surgical tool for suturing an epicardial pacer electrode to the heart without a thoracotomy and with a minimum degree of trauma to the heart tissue at the point of electrical contact.

Another object is to provide a surgical tool that can form sutures in generally inaccessible tissue that is not directly visible.

Yet another object is to provide a surgical tool with the foregoing advantages that can form multiple sutures at the same time.

A further object is to provide a pacer electrode suturing tool that guides the electrode and its lead to the implantation site and selectively detaches both the electrode and its lead after the suture is formed.

A still further object is to provide a suturing tool which is reliable, convenient to use, and of relatively simple and inexpensive construction.

SUMMARY OF THE INVENTION

A surgical tool for forming at least one generally circular suture within normally inaccessible tissue has an elongated body with a grip and plunger actuator at one end. In a preferred form the other or distal end is adapted to releasably hold an epicardial pacer electrode. The body supports at least one tubular die member with an inner bore shaped for closely guiding an associated, formable suture element. The end of the die member adjacent the electrode is curved to deflect the suture element beyond its elastic limit, thereby imparting a curvature of an essentially predetermined radius to the suture element. The plunger and a push wire carried in the die member drive the suture element through the bore and past its curved deflecting end. This action ejects the suture element along a curving path to form a substantially closed-loop, circular suture. The suture or sutures thus formed pass through the heart tissue adjacent the electrode and securely hold the epicardial pacer electrode in electrical connection with the heart tissue.

In a preferred embodiment, two tubular die members are employed, arranged on opposite sides of the electrical connection element of the electrode, and each carrying at its distal end one suture element. The distal end of the tool body has an interior recess adapted to receive a resiliently deformable plug on the rear face of the electrode. When the plug is seated in the recess, the suturing tool can direct the electrode to an implantation site on the heart muscle. The distal end of the body and the attached electrode are preferably slanted with respect to the longitudinal axis of the body to facilitate placement and implantation of the electrode. The body also has a generally low cross-sectional height to facilitate its passage under the rib cage of a patient.

A slot in the underside of the suturing tool receives and grips an electrical lead from the pacer electrode to the pacer electronics. This immobilizes the lead and prevents it from interferring with the insertion or implantation procedures. When the pacer electrode is properly positioned on the heart, a forward movement of the plunger over a first portion of its travel ejects the two suture elements which penetrate the heart tissue to secure the electrode to the heart. A further forward movement of the plunger and an axially slideable separating rod pushes the resilient electrode plug out of the tool recess to detach the pacer electrode from the tool. The forward movement of the separating rod also cams the electrode leads from the slot in the underside of the tool. Preferably a portion of the slot is formed by a recess in the separating rod and the cam is an inclined rear surface of the recess.

These and other features and objects will become apparent to those skilled in the art from the following detailed description which should be read in light of the accompanying drawings.

BRIEF DESCRIPTION OF THE DRAWINGS

FIG. 1 is a top plan view of a suturing tool according to this invention adapted to secure an epicardial pacer electrode to a heart;

FIG. 2 is a view in side elevation of the tool and electrode shown in FIG. 1;

FIG. 3 is an enlarged view in section taken along the line 3—3 in FIG. 1;

FIG. 4 is a bottom plan view with portions broken away corresponding to FIG. 3 and showing a slot in the underside of the tool for releasably securing the electrode lead;

FIG. 5 is a view in section taken along the line 5—5 of FIG. 2;

FIG. 6 is a detail view in section and partially in elevation of the electrode and the adjacent portions of the tool taken along the line 6—6 of FIG. 1;

FIG. 7 is a view in section taken along the line 7—7 in FIG. 6;

FIG. 8 is a view in end elevation corresponding to FIG. 7 of the suturing tool;

FIG. 9 is a view in section taken along the line 9—9 in FIG. 6;

FIG. 10 is a detail view in side elevation of one die member;

FIG. 11 is a top plan view of the electrode; and

FIG. 12 is a view in front elevation of the electrode shown in FIG. 11

DETAILED DESCRIPTION OF THE PREFERRED EMBODIMENTS

FIGS. 1 and 2 show a surgical suturing tool 12 constructed according to the invention and particularly adapted to suture an epicardial pacer electrode 18 to a heart. The tool 12 has a generally elongated body 14 preferably formed of a rigid molded plastic such as polycarbonate. One end 12a of the tool has a pistol-like handle 16 that allows a surgeon to grip the tool comfortably, guide it accurately and operate it easily during the suturing procedure. The other distal end or head 12b of the tool is adapted to hold the epicardial pacer electrode 18 and guide it to the desired attachment point on the heart. A hand operated plunger 20 slides axially in a recess 22 within handle 16. The plunger travels between a retracted position and a full forward position. During a first portion of its forward travel (to the right as shown) the plunger sutures the electrode to the heart. During a second portion of its forward travel, the plunger detaches the electrode and its electrical lead 40 from the tool 12.

The plunger 20 has two extension arms 24, 24 which slide axially in die passages 26, 26. The die passages 26, 26 are circular in cross section and extend the full length of the body 14 from the handle 16 to the end face 12c. They may be formed of stainless steel hypodermic tubing. These passages closely guide the extension arms 24, 24 as well as pusher wires 28, 28 and suture elements 30, 30 held in the die passages. The pusher wires 28, 28 are relatively stiff, preferably formed of 0.010 diameter stainless steel. The suture elements 30, 30 are formed of a suitable malleable material which will retain a set after being stressed byond its elastic limit, preferably half-hard elgiloy. Each extension arm 24 is associated with and axially aligned with one pusher wire 28 and one suture 30. These elements are in end-abutting relationship so that a forward movement of the plunger from its retracted position is translated into a corresponding movement of the associated wire and suture within the surrounding die passage 26.

With particular reference to FIGS. 6–10, the distal ends 26a, 26a of the die passages 26, 26 within the head portion 12b of the tool are curved so that suture elements 30, 30 emerge from the die passages 26, 26 following an arcuate path 31 whose curvature is determined by the curvature of the die passages ends 26a, 26a. The curvature of the ends 26a, 26a is selected so that operation of the plunger drives the suture elements to penetrate heart tissue first at 32 (FIG. 6), then at 34, and finally through notches 36 (FIGS. 6 and 12) in pacer electrode 18. The lengths of suture elements are sufficient to form closed-loop circular sutures that reliably secure the electrode to the heart with a projecting electrical stimulation electrode 38 of the electrode 18 implanted in the heart tissue. The projecting electrode 38 is of conventional design and includes a cutting member 38a and a coiled conductor 38b that supports the cutting member and transmits a heart stimulating electrical signal from a pacer (not shown) to the heart muscle. An electrical lead 40 transmits the signal from an implanted pacer (not shown) to the projecting electrode 38. It should be noted that a significant advantage of this invention is that the trauma caused by suturing is isolated from the point of electrical stimulation. Another significant advantage is that the invention in its preferred form forms two closed-loop sutures to secure the electrode to the heart with a high degree of reliability.

The electrode is releasably secured on the inclined end face 12c of the tool head 12b. The tool 12 is therefore useful not only in suturing, but also in guiding the electrode to the proper location on the heart, usually following a path under the rib cage from an incision in the abdomen where the pacer is implanted. The overall geometry of the tool 12 is also so that it facilitates this insertion procedure. The length is selected so that the handle 16 and the plunger 20 are readily grasped and manipulated when the electrode is positioned on the heart. The cross-sectional width of the tool body is greater than the height (FIGS. 5 and 9) to slide under the rib cage. The head 12b and the electrode 18 mounted flush against the end face of the head are tilted downwardly so that the electrode 18 is generally abuts the adjacent heart tissue at the implantation site. This tilt also slants the electrode lead 40 projecting from the lower edge of the electrode 18 to facilitate the insertion of the electrode. The handle 16 is horizontally oriented to minimize its interference with the insertion.

With particular reference to FIGS. 7 and 11, the electrode 18 has a resilient protrustion 42 with an enlarged, generally cylindrical end portion 42a adapted to seat in a generally cylindrical recess 44 formed in the head 12b of the tool. The electrode is secured on the tool by pressing the protrusion 42 into a narrowed distal end 46a of a central channel 46 in the body 14 until the portion 42a seats in the recess 44. A separating element or rod 48, preferably formed of a rigid molded plastic, slides axially in the channel 46 which extends from the recess 22 in the handle 16 to the end face 12c of the tool lead. As shown in FIGS. 1 and 2, one end 48a of the rod is adapted to engage the plunger 20. The other end 48b is of reduced width and adapted to engage the resilient protrusion 42 of the electrode when it is seated in the recess 44. During the first portion of the travel of the plunger from the fully retracted position, it acts through the extensions 24, 24 and the pusher wires 28, 28 to drive and eject the circular sutures. At the end of the second portion of the travel the rod pushes the protrusion 42 out of the recess 44 and thereby detaches the electrode 18 from the tool 12. The last portion of the travel also completes the ejection of the sutures. The initial position of the rod 48 is shown in solid lines in FIG. 3 and the full forward position is shown in phantom.

With reference to FIGS. 2-4, the rod 48 also operates to detach the lead 40 which is held in part in a slot 50 defined by an opening 52 in the bottom wall of the body 14 and a recess 54 formed in the rod 46. When the plunger is fully retracted, the recess 54 overlies the slot 52. They together receive a portion 40a (FIGS. 2 and 5) of the lead. The side walls 52a, 52a of the opening 52 are upwardly narrowing to promote the insertion of the lead into the slot but block its movement out of the slot once it is fully inserted as is best seen in FIG. 5. This immobilizes the lead during insertion and minimizes the likelihood that it will interfere with the insertion or suturing operations. When the suturing is completed, the forward sliding movement of the rod 48 causes a sloped cam surface 56 at the rear of the recess 54 to engage the lead and drive it out of the slot 50. The lead is thus released from the tool just before the electrode is detached.

To prepare the suturing tool 12 for operation, the plunger 20 is removed and the suture elements 30, 30 are each inserted into one of the die passages 26, 26 through the handle recess 22. Next, the pusher wires 28, 28 are inserted into the passages 26, 26 in the same manner. The separating rod 48 is inserted into the channel 46 with the recess 54 aligned with the slot 52 in the tool body. The plunger 20 is replaced in the recess 22. Finally, the pacer electrode is fixed on the head 12b and the head portion 40a is jammed into the slot 50. The tool is then ready for use.

Using a small incision below the rib cage, the tool carrying the electrode is inserted into the body and guides the electrode to the heart by mediastinoscopy. When the electrode is in the proper location, the plunger is pushed forward. The first portion of its travel ejects and forms the suture elements 30, 30 into closed-loop circular sutures that permanently attach the electrode to the heart. In the last portion of its travel, the separating rod ejects the electrode and its leads from the suturing tool. The tool is then withdrawn, leaving the pacer electrode attached to the heart. Prior to actually applying the electrode to the heart, the tool with the probe can be utilized for exploring or mapping the heart with regard to sensitivity. This is advantageous as compared with mapping initially with a separate probe because of the difficulty of returning exactly to the same spot with a separate electrode.

There has been described a surgical tool that sutures an epicardial pacer electrode to the heart without the need of directly exposing the heart by a thoracotomy which is a substantially more hazardous procedure than a small incision below the rib cage. Also, the present invention sutures the pacer electrode to the heart with the sutures spaced from the point of electrical contact with heart tissue to minimize trauma. Furthermore, these objects and advantages are achieved by means of a tool of simple and inexpensive construction.

Although the suture forming tool disclosed herein has particular utility in attaching an epicardial pacer electrode to the heart, it should be understood that the tool may be advantageously applied to other medical procedures since the tool allows the formation of closed loop sutures at remote locations within the body. A tissue tear may be repaired, for example, without the necessity of fully exposing the site as would be required with conventional suturing techniques. Also, while the invention has been described with reference to a tool for forming a pair of sutures, it can readily be adapted to form only one or more than two sutures. These and other modifications of the invention will occur to those skilled in the art from the foregoing detailed description and the accompanying drawings. Such modifications are intended to fall within the scope of the appended claims.

What is claimed is:

1. A surgical tool for forming a pair of circular sutures to secure an epicardial pacer electrode with an electrical lead to a heart with the sutures spaced from the point of electrical connection between the electrode and the heart, comprising an elongated body, a pair of formable suture elements, a pair of tubular guide members mounted in said body and extending generally along the longitudinal axis of said body, said guide members each having an inner bore shaped for closely guiding one of said suture elements through an axial sliding movement that ejects said one suture element from one end of said body and each including a curved section disposed at said one body end for deflecting said one suture element beyond its elastic limit to impart a curvature of a substantially predetermined radious to the ejected portion of said one suture element, plunger means axially slidable within said body for driving said pair of suture elements in said axial sliding movement through said bores and past said curved section to affect said ejection along a path curving at substantially said predetermined radius, the length of each of said suture elements being sufficient to form a substantially closed-loop suture when fully ejected, a pair of pusher wires operatively connected between said plunger means and said pair of suture elements, means for replaceably supporting said electrode at said one body end, a member axially slidable in said body and operatively connected between said plunger means and said supporting means, said member being structured to detach said electrode as said suture is fully ejected, means for replaceably holding a portion of said lead that is spaced from said electrode and means for releasing said lead.

2. A surgical tool for forming a circular suture to secure an epicardial pacer electrode to a heart, comprising an elongated body, a formable suture element, a tubular guide member mounted in said body, said guide member having an inner bore shaped for closely guiding said suture element through an axial sliding movement that ejects said suture element from one end of said body, and including means for deflecting said suture element beyond its elastic limit to impart a curvature of a predetermined radius to the ejected portion of said suture element, means for driving said suture element in said axial sliding movement through said bore and past said deflecting means to effect said ejection along a path curving at substantially said predetermined radius, said suture element forming a substantially closed-loop suture when fully ejected, means for replaceably supporting said electrode at said one body end, and means for detaching said electrode after said suture is fully ejected.

3. A surgical tool according to claim 2 wherein said electrode includes an electrical lead and further comprising means for replaceably holding a portion of said lead that is spaced from said electrode.

4. A surgical tool according to claim 3 wherein said detaching means includes means for releasing said lead.

5. A surgical tool according to claim 4 wherein said driving means includes plunger means axially slidable within said body and means for operatively connecting said plunger and said suture element.

6. A surgical tool according to claim 5 wherein said connecting means includes a pusher wire carried in said guide member and extending between said plunger means and said suture element.

7. A surgical tool according to claim 5 wherein said electrode has a resilient connecting member and wherein said electrode support means comprises a recess formed in said one body end and adapted to engage said resilient connecting member.

8. A surgical tool according to claim 7 wherein said detaching means includes a member axially slidable in said body and operatively connected between said plunger means and said resilient connecting means.

9. A surgical tool according to claim 8 wherein said plunger means is operatively connected to said suture element throughout said axial sliding and is operatively connected to said slidable member during a final portion of said sliding.

10. A surgical tool according to claim 8 wherein said lead holding means comprises an opening formed in said body and a recess formed in said slidable member and aligned with said opening when said plunger is in a retracted position.

11. A surgical tool according to claim 10 wherein said recess has a cam surface adapted to drive said lead from said recess and said opening when said slidable member slides toward said one body end.

* * * * *